US00PP18898P2

(12) United States Plant Patent
Eskelund

(10) Patent No.: US PP18,898 P2
(45) Date of Patent: Jun. 10, 2008

(54) ROSE PLANT NAMED 'EVERA 122'

(50) Latin Name: *Rosa hybrida*
Varietal Denomination: Evera 122

(75) Inventor: Rosa Eskelund, Fåborg (DK)

(73) Assignee: Roses Forever ApS, Fåborg (DK)

( * ) Notice: Subject to any disclaimer, the term of this patent is extended or adjusted under 35 U.S.C. 154(b) by 0 days.

(21) Appl. No.: 11/700,607

(22) Filed: Jan. 30, 2007

(51) Int. Cl.
*A01H 5/00* (2006.01)

(52) U.S. Cl. ..... Plt./137

(58) Field of Classification Search ..... Plt./137
See application file for complete search history.

*Primary Examiner*—Annette H Para
(74) *Attorney, Agent, or Firm*—C. A. Whealy

(57) ABSTRACT

A new and distinct cultivar of Rose plant named 'Evera 122', characterized by its upright and rounded plant habit; dark green-colored leaflets; freely branching growth habit; freely flowering habit; large double pink-colored flowers; flowers held upright on strong and erect peduncles; and good postproduction longevity.

1 Drawing Sheet

Botanical designation: *Rosa hybrida.*
Cultivar denomination: 'EVERA 122'.

BACKGROUND OF THE INVENTION

The present Invention relates to a new and distinct cultivar of Rose plant, botanically known as *Rosa hybrida,* commercially used as a potted Rose, and hereinafter referred to by the name 'Evera 122'.

The new Rose is a product of a planned breeding program conducted by the Inventor in Fåborg, Denmark. The objective of the breeding program was to develop new potted Rose varieties with novel and attractive flower colors, disease resistance and excellent postproduction longevity.

The new cultivar originated from a cross-pollination made by the Inventor on Jun. 1, 2003 of a proprietary Rose selection identified as code number 01-0127, not patented, as the female, or seed, parent with an unnamed Rose selection, not patented, as the male, or pollen, parent. The cultivar Evera 122 was discovered and selected by the Inventor in on Aug. 20, 2004 as a single flowering plant within the progeny of the stated cross-pollination in a controlled environment in Fåborg, Denmark.

Asexual reproduction of the new Rose by cuttings at Fåborg, Denmark since Feb. 1, 2005, has shown that the unique features of this new Rose are stable and reproduced true to type in successive generations of asexual reproduction.

SUMMARY OF THE INVENTION

The following traits have been repeatedly observed and are determined to be the unique characteristics of 'Evera 122'. These characteristics in combination distinguish 'Evera 122' as a new and distinct cultivar:

1. Upright and rounded plant habit.
2. Dark green-colored leaflets.
3. Freely branching growth habit.
4. Freely flowering habit.
5. Large double pink-colored flowers.

6. Flowers held upright on strong and erect peduncles.
7. Good postproduction longevity.

Plants of the new Rose differ from plants of the parent selections in the following characteristics:

1. Plants of the new Rose and the parent selections differ in plant habit.
2. Plants of the new Rose and the parent selections differ in flower color.

Plants of the new Rose can be compared to plants of the Rose cultivar Evera 134, disclosed in U.S. Plant Pat. No. 17,030. In side-by-side comparisons conducted in Fåborg, Denmark, plants of the new Rose differed from plants of the cultivar Evera 134 in the following characteristics:

1. Plants of the new Rose had broader leaves than plants of the cultivar Evera 134.
2. Plants of the new Rose had more petals and pistils per flower than plants of the cultivar Evera 134.
3. Plants of the new Rose were not fragrant whereas plants of the cultivar Evera 134 were slightly fragrant.
4. Plants of the new Rose and the cultivar Evera 134 differed in flower color.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the top of the sheet comprises a side perspective view of a typical plant of 'Evera 122' grown in a container.

The photograph at the bottom of the sheet is a close-up view of a typical flower of 'Evera 122'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown during the summer and early autumn in Fåborg, Denmark, in a glass-covered greenhouse and under commercial production practices. Plants were pinched one time and were about 12 to 14 weeks old when the photographs and description were taken. During the production of the plants, day temperatures averaged 22° C., night temperatures averaged 21° C., and light levels were about 20,000 lux. In the following description, color references are made to The Royal Horticultural Society Colour Chart, 2001 Edition, except where general terms of ordinary dictionary significance are used.

Botanical classification: *Rosa hybrida* cultivar Evera 122

Parentage:

*Female, or seed, parent.*—Proprietary seedling selection of *Rosa hybrida* identified as code number 01-0127, not patented.

*Male, or pollen, parent.*—Unnamed selection of *Rosa hybrida,* not patented.

Propagation:

*Type.*—By cuttings.

*Time to initiate roots.*—About ten to twelve days at 24° C.

*Time to produce a rooted young plant.*—About one month at 24° C.

*Root description.*—Fibrous, medium thickness; white in color.

*Rooting habit.*—Freely branching; moderately dense.

Plant description:

*Plant form.*—Upright and rounded plant habit.

*Growth habit.*—Moderately vigorous growth habit. Freely branching habit; about two to four lateral branches develop from the pinching; dense and bushy growth habit.

*Plant height.*—About 23 cm.

*Plant width* (*spread*).—About 18 cm to 20 cm.

*Lateral branches.*—Length: About 16 cm to 20 cm. Diameter: About 3 mm. Internode length: About 2 cm to 3 cm. Strength: Strong. Texture: Smooth, glabrous. Color: Close to 146A. Thorns: Density: About one per linear cm. Shape: Triangular with sharp acuminate apices. Height: About 2 mm to 5 mm. Diameter, at base: About 1 mm to 2 mm. Color, immature: Close to 145B. Color, mature: Close to 162B.

Foliage description:

*Arrangement.*—Alternate; compound with three to five leaflets per leaf.

*Leaf length.*—About 7.5 cm to 9.5 cm.

*Terminal leaflet length.*—About 4.5 cm.

*Lateral leaflet length.*—About 3 cm to 3.5 cm.

*Leaf width.*—About 7 cm to 8 cm.

*Terminal leaflet width.*—About 2.5 cm to 3 cm.

*Lateral leaflet width.*—About 1.8 cm. to 2.6 cm.

*Leaflet shape.*—Ovate.

*Leaflet apex.*—Acuminate.

*Leaflet base.*—Obtuse.

*Leaflet margin.*—Biserrulate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 137C; margins tinged with close to 59A. Developing leaflets, lower surface: Close to 146B; margins tinged with close to 59A. Fully expanded leaflets, upper surface: Darker than 147A; venation, close to 146C. Fully expanded leaflets, lower surface: Darker than 191A; venation, close to 146C.

*Petioles.*—Leaf petiole length: About 2 cm to 2.5 cm. Leaflet petiole length: About 1 mm to 2 mm. Leaf petiole diameter: About 1 mm. Leaflet petiole diameter: About 1 mm. Leaf petiole texture, upper surface: Rough. Leaf petiole texture, lower surface: Smooth. Leaflet petiole texture, upper and lower surfaces: Smooth. Leaf and leaflet petiole color, upper and lower surfaces: Close to 146B.

*Stipules.*—Quantity: Two per leaf. Length: About 5 mm. Width: About 1 mm. Shape: Lanceolate. Apex: Acuminate. Base: Truncate. Margin: Serrate. Texture, upper and lower surfaces: Leathery. Color, upper surface: Close to 137A. Color, lower surface: Close to 137B to 137C.

Flower description:

*Flower type and habit.*—Large double pink-colored flowers with numerous petals. Consistently symmetrical rosette flowers. Flowers borne singly on erect and strong peduncles; one terminal flower per lateral branch. Flowers persistent.

*Flowering season.*—Year-round under greenhouse conditions, optimal flowering from spring through autumn under garden conditions; flowering intermittent.

*Flower diameter.*—About 5 cm to 6 cm.

*Flower depth* (*height*).—About 3 cm.

*Flower longevity on plant.*—About two weeks.

*Fragrance.*—None detected.

*Flower buds* (*at stage of showing color*).—Shape: Ovoid. Length: About 1.5 cm. Diameter: About 1 cm. Color: Closest to 144A to 146B.

*Petals.*—Quantity: Numerous; about 58 per flower. Length: About 2.5 cm to 3 cm. Width: About 2.2 cm to 3.5 cm. Shape: Broadly obovate. Apex: Rounded and retuse. Base: Attenuate. Margin: Entire. Texture, upper and lower surfaces: Smooth, glabrous; satiny. Color: When opening, upper surface: Close to 65A; towards the margin, close to 55D. When opening, lower surface: Close to 55B; towards the margin, close to 55D. Fully opened, upper and lower surfaces: Close to 65A; towards the margin, close to 65D; color becoming closer to 65D with development.

*Sepals.*—Quantity per flower: Typically five. Length: About 3 cm. Width: About 7 mm. Shape: Linear to lanceolate. Apex: Sharply pointed. Base: Truncate. Texture, upper and lower surfaces: Pubescent. Color: When opening, upper surface: Close to 138A to 191A. When opening, lower surface: Close to 143A. Fully opened, upper surface: Close to 191A. Fully opened, lower surface: Close to 143A.

*Peduncles.*—Strength: Strong, but flexible. Aspect: Mostly erect. Length: About 2.5 cm to 4 cm. Diameter: About 3 mm. Texture: Rough. Color: Close to 144A.

*Reproductive organs.*—Stamens: Quantity: About 120 per flower. Anther length: About 2 mm. Anther shape: Reniform. Anther color: Close to 15A. Filament color: Close to 154D. Pollen amount: None observed. Pistils: Quantity: About 125 per flower. Pistil length: About 2 mm. Stigma color: Close to 5C. Style length: About 3 mm to 5 mm. Style color: Close to 145D. Receptacle shape: Cup-shaped. Receptacle height: About 7 mm. Receptacle diameter: About 8 mm to 9 mm. Receptacle texture: Smooth, glabrous. Receptacle color: Close to 144C. Seed/fruit: Seed and fruit production has not been observed.

Pathogen/pest resistance: Plants of the new Rose have not been observed to be resistant to pathogens and pests common to Roses.

It is claimed:

1. A new and distinct Rose plant named 'Evera 122' as illustrated and described.

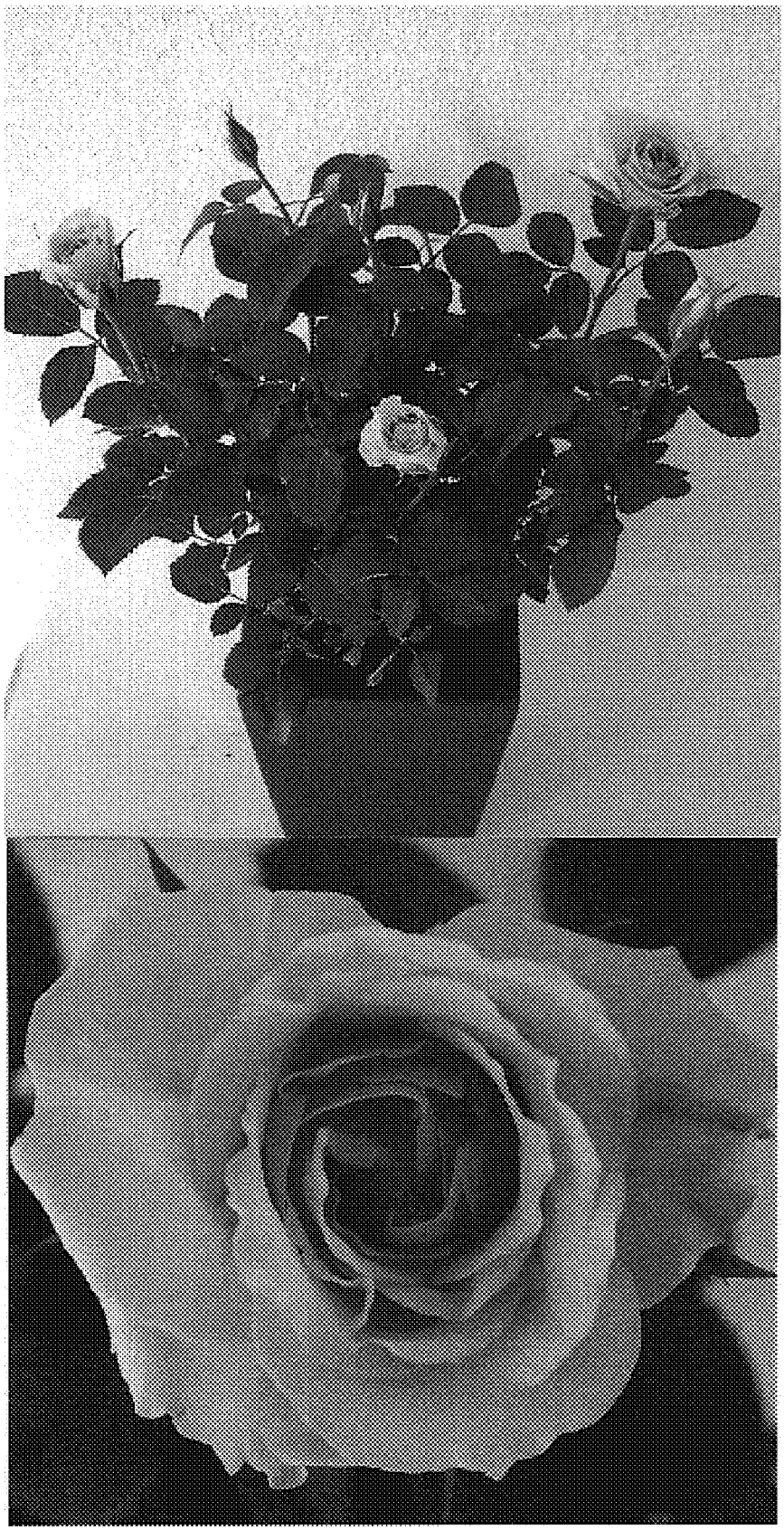

* * * * *